United States Patent [19]

John

[11] Patent Number: 4,974,598

[45] Date of Patent: Dec. 4, 1990

[54] EKG SYSTEM AND METHOD USING STATISTICAL ANALYSIS OF HEARTBEATS AND TOPOGRAPHIC MAPPING OF BODY SURFACE POTENTIALS

[75] Inventor: Erwin R. John, Mamaroneck, N.Y.

[73] Assignee: Heart Map, Inc., New York, N.Y.

[21] Appl. No.: 329,583

[22] Filed: Mar. 28, 1989

Related U.S. Application Data

[63] Continuation-in-part of Ser. No. 185,031, Apr. 22, 1988, abandoned.

[51] Int. Cl.$^5$ .............................................. A61N 1/00
[52] U.S. Cl. .................................... 128/696; 128/700; 128/702; 264/413.06
[58] Field of Search ............... 128/695, 696, 700, 702, 128/703, 704, 705, 706, 709; 364/413.05, 413.06

[56] References Cited

U.S. PATENT DOCUMENTS

| | | | |
|---|---|---|---|
| 3,832,994 | 8/1974 | Bicher et al. | 128/2.06 A |
| 4,023,564 | 5/1977 | Valiquette et al. | 128/2.06 A |
| 4,193,393 | 2/1980 | Schlager | 128/710 |
| 4,416,288 | 11/1983 | Freeman | 364/413.05 |
| 4,531,527 | 7/1985 | Reinhold, Jr. et al. | 128/696 |
| 4,570,225 | 2/1986 | Lundy | 364/413.05 |
| 4,679,144 | 7/1987 | Cox et al. | 364/417 |
| 4,732,158 | 3/1988 | Sadeh | 364/413.06 |
| 4,812,976 | 3/1989 | Lundy | 364/413.06 |

Primary Examiner—Francis Jaworski
Assistant Examiner—George Manuel
Attorney, Agent, or Firm—Eliot S. Gerber

[57] ABSTRACT

The Heart State Analyzer (HSA) is a system and method in medical non-invasive electrocardiographic (EKG) analysis of human heart beats for the early detection of certain heart diseases in which a large number of electrodes, for example, 32 to 64, are attached on the chest, back and sides of the patient, i.e., "body surface". The electrical signals detected by the electrodes ae converted to digital data, treated to remove muscle artifact and other noise, and then analyzed mathematically to determine the presence or absence of abnormal body surface potential distributions, or of unusual beat morphologies, compared statistically to the self-norm "typical beat" of the patient and also compared to a data base compiled from comparable normal population groups. The results of the statistical analysis are displayed as topographical maps of the body surface, color coded to represent the presence of significant derivations from the norms, defined as "abnormality", i.e., abnormal spatio-temporal patterns of voltages on the body surface, or as waveshape or histogram displays of features, similarly Z-transformed and color coded. Discriminant functions, stored in the heart state analyzer, estimate the relative probability of various cardiac pathologies.

23 Claims, 3 Drawing Sheets

EKG SYSTEM AND METHOD USING STATISTICAL ANALYSIS OF HEARTBEATS AND TOPOGRAPHIC MAPPING OF BODY SURFACE POTENTIALS

BACKGROUND OF THE INVENTION

1. Field of the Invention

The present invention, called the Heart State Analyzer (HSA), relates to medical instruments and more particularly to the detection and analysis of human heart beat waves by a non-invasive EKG (electrocardiograph or "ECG") system and method.

2. Description of the Related Art

In the human heart a wave of depolarization is initiated by a spontaneous electrical impulse in a local region at the top of the heart, called the sinoatrial node or pacemaker. That depolarization wave causes a contraction of the heart muscle, as it moves down the heart, and causes pumping of the blood. The ordered contraction of the heart muscle depends upon the integrity of the electrical conduction system (including the "His-Purhinge" fibers) and an adequate supply of blood to the heart from a small number of major coronary arteries, which are the blood vessels leading to the heart. The failure of the heart to receive an adequate supply of blood ("ischemia") may result in the symptoms of angina pectoris, myocardial infarction and even death. Although the present invention is described as being useful in connection with the early detection of silent ischemia, and ischemia in general, it will be understood that further research using the Heart State Analyzer will disclose other heart diseases and abnormalities that it may detect or analyze. Heart disease is the leading cause of death in men in the United States over thirty years of age.

A type of coronary artery disease, in which there are periods when the heart does not receive a sufficient blood supply ("myocardial ischemia") is a major cause of heart attacks. It causes injury or death to large numbers of persons without prior symptoms of heart disease, such as prior attacks of angina pectoris, myocardial infarction, or abnormal finding on the conventional EKG.

The most common cause of a heart attack is that one or more of the major coronary arteries to the heart is suddenly blocked. Such sudden blockage generally occurs in a patient affected with "coronary atherosclerosis", a narrowing of the arteries due to "plaque", which is an accumulation of excess cellular and connective tissue and cholesterol. Such blockage may be sudden and catastrophic, for example, because of a spasm or because a blood clot blocks the restricted artery. A second cause of heart attack is the gradual occlusion of the opening (lumen) of the artery by plaque deposits, i.e., "stenosis" of one or more coronary arteries.

One conventional non-invasive method of determining the presence of heart disease is, in effect, to provoke certain of its symptoms, such as angina pain or abnormal EKG signs by a "stress test" in which the patient walks rapidly on a treadmill. The stress test is controversial and inconclusive. In a certain number of cases it causes heart attacks and, in addition, some patients who pass the stress test without displaying chest pain or EKG abnormalities nevertheless prove to have heart disease. Another non-invasive method of diagnosis utilizes "PET" (positronemission tomograph) images. A cross-sectional image of regional metabolism is displayed in a color-coded CRT representing the gamma radiation given off in the collison of electrons in cell with positrons emitted by radionuclides incorporated into metabolic substances. However, such imagery is expensive, time consuming, is not generally availble and may be difficult to interpret.

Various types of devices are commercially available, or have been suggested in the patent or medical literature, for the monitoring of EKG signals.

U.S. Pat. No. 4,679,144 to Cox et al relates to a programmable apparatus worn by a patient during the day and performing continuous real-time analysis of EKG signals. It uses the conventional placement of leads.

Other patents and articles cited in the Cox et al patent relate to other computer-based EKG systems. In U.S. Pat. No. 4,193,333 to Schlager, which utilizes twelve leads, the "R" wave peak of each heart beat is detected and initiates the timing. Digital memory addresses are assigned as 256 time segments to components of the EKG wave, which are compared to preset references.

In "body surface mapping", a large number of unipolar EKG leads, for example 87, are attached to the patient's body using a body surface potential mapping system (e.g., Model HMPM-51005 of Chunchi Denish Co., Japan), see Ikeda et al, "Detection of Posterior Myocardial Infarction By Body Surface Electrocardiographic Mapping After Dipyridamole Infusion", *J. Electrocardiology* 19(3), 1986, 213–224. The map displayed by such systems is not the result of a mathematical or statistical analysis of the data. Interpolation is subjective, and the map may be difficult to interpret.

A series of articles authored by Robert L. Lux and others of the College of Medicine, University of Utah, relate to isopotential maps using a large number of ECG leads. The articles Lux et al, "Redundancy" I "Spatial compression" and II "Temporal compression" *Cir. Res.* 49, 186 and 197 (1981) explain that the 192 leads (body surface electrocardiograms) may be reduced to 12 coefficient waveforms, a data compression of 16:1. Further, the data may be compressed 20:1 using "K-L" expansion. The system provides QRST maps of individual subjects characterized by 216 numbers (coefficients), see Green, Lux et al, "Detection and localization of coronary artery disease with body surface mapping in patients with normal electrocardiograms", *Circulation* 76, No. 6, 1290–1297 (1987—non-prior art).

OBJECTIVES AND FEATURES OF THE INVENTION

It is an objective of the present invention to provide a system and method for the determination of the presence, or absence, of heart disease among a broader population than those who would be presently recommended to take a stress test, to more accurately determine heart disease or its absence than the stress test, and to make such determination without the danger and patient effort of a stress test or invasive methods.

It is a further objective of the present invention to provide such a system and method which is non-invasive and utilizes removable and painless electrodes which contact the skin.

It is a further objective of the present invention to provide such a system and method which is based upon objective statistical measures and computer analysis of data and does not depend upon reading and subjective interpretation by specialized medical personnel of analog EKG waveforms or of topographic maps of body surface potentials or isopotential contours.

It is a further objective of the present invention to provide such a system and method which may be applied to a patient and the tests performed, using medical personnel other than physicians, such as nurses or medical technicians, although the analysis of the test results would be by physicians or other highly trained medical personnel.

It is a further objective of the present invention to provide such a system and method in which the testing procedures would be relatively simple to perform, the analyses automatic, and the results presented in a relatively simple and clear format, so that the chances of ambiguous conclusions are minimized.

It is a further objective of the present invention to provide such a system and method which may be implemented using relatively low cost and reliable components, so that the system may be economical to manufacture and the costs of the test kept low.

It is a further objective of the present invention to provide such a system and method in which the testing procedures and data analysis are relatively rapid and testing and interpretation may take place in the physician's office or hospital as part of a routine physical examination.

It is a feature of the present invention to provide an electrocardiograph EKG system and method to detect heart beats (having P, Q, R, S, T and U portions), for the detection of heart disease in some but not all patients, as well as those heart beats not having P, Q, R, S, T and U portions.

Electrodes to detect heart activity electrical signals are connected to the skin of the patient in separated locations around the heart on the chest, sides and back of the patient (torso). The electrical signals detected at each electrode are amplified by amplification means and converted into ECG digital data by digital conversion means.

Norm storage means receive and store normal digital data representing normal or abnormal ECG heart activity electrical signal during the time of the cardiac cycle. The system and method is characterized by automatic digital computer statistical analysis means to operate in the space-time domain defined by the space of the torso and the time of the cardiac cycle and the frequency domain to analyze the said digital data on a statistical basis compared to the stored normal data.

The space-time domain analysis includes means to construct homogenous subclasses; means to extract univariate features selected from the group of the P-Q, Q-R, R-S, S-T, T-U or R-R intervals, P, QRS, T or U amplitude, P, QR, QRS, T or U power.

In the space-time domain, defined as the space of the torso of the patient and the time of the cardiac cycle, the analysis is as follows:

Where $EKG_i(t)$ is the voltage of the cardiac cycle at position i; and $a_{ij}$ is the "factor score" defining the contribution of factor to $EKG_i'$ and $F_j(t)$ is the waveshape of factor j throughout the cardic cycle (factor j being a selected component of the EKG waveform); and $Z_{ij}$ is the Z transform of $a_{ij}$ and $M_{ij}$ is the mean and $6_{ij}$ is the variance for each $a_{ij}$ and all $F_j(t)$; then $$EKG_i(t) = \sum_{j=1}^{K} a_{ij} F_j(t)$$

-continued

Use $Z_{ij} = \dfrac{a_{ij} - M_{ij}}{6_{ij}}$ so that $$EKG_i(t) = \sum_{j=1}^{K} Z_{ij} F_j(t)$$

$Z_{ij}$, at each topographic map position corresponding to an electrode lead, is encoded to reflect probability that $a_{ij}$ is within the normal range. Preferably the encloding is a color code with color-coded interpolations between the lead positions to provide a color-coded map of the torso. A different color-coded map is generated for each $F_j$ (waveshape of factor j). Then the loci of significant factor Z-score is input to a discriminant function to ascertain the *type* of coronary disease and the integral of the deviant surface area is computed to estimate the *severity* of the impairment.

Display means, such as a color CRT monitor, is used to display the factor Z-scores on a topographic map representing the torso of the patient, each map location corresponding to the location of the corresponding electrode.

BRIEF DESCRIPTION OF THE DRAWINGS

Other objectives and features of the present invention will be apparent from the following detailed description of the inventor's presently known best mode, taken in conjunction with the accompanying drawings. In the drawings.

DETAILED DESCRIPTION OF THE INVENTION

1. Introduction and System Overview

The heart is a hollow muscular organ, provided with one-way valves, which rhythmically contracts to pump blood in one direction. The blood is recived in a chamber called the atrium (auricle) and is pumped out from a chamber called the ventricle.

A region of the heart may be impaired or "marginal", in the sense that the region fails to function properly, displaying diminished vigor or amounts of contraction. Such regions of the heart are characterized electrically by a slower rate of depolarization or repolarization, or by a smaller potential change as the wave of depolarization reaches the affected region, indicating partial depolarization in the deseased region. Such slower speed, lower amplitude, or partial depolarization in a region appear as abnormal spatiotemporal patterns of voltage on the surfaces of the torso ("body surface potentials") during the contractions of the heart. Such abnormalities may be present during each contraction of the heart, or may only appear intermittently, during "unusual" or atypical beats.

The purpose of the present invention is to detect, by statistical methods, abnormal body surface potential distributions on the torso of an individual patient by comparison with normative data derived from a reference group of healthy persons. Since such abnormalities may only be present during certain beats, the invention includes means to detect normal and unusual beats by comparing the morphology of every single beat with the average beat of the individual and with the average beat of the segment of the normal population to which the individual belongs, for example, a group of healthy non-smoking United States males between the ages of 30 and 35. These various comparisons are performed in the *time domain*, examining the spatio-temporal distribution of voltages, and in the *frequency domain*, examining the distribution of potentials at various frequencies and in various phase relationships across the body surfaces. Abnormal body surface distributions of these extracted features of the ECG signal are correlated with impaired perfusion of particular regions of heart muscle by partial occlusion of different heart arteries which supply blood to those regions, and other manifestations of artial or ventricular origin. Thus, a goal of this invention is to permit non-invasive diagnosis of coronary artery disease ("CAD") and/or other atrial or ventricular disease in the resting patient by using discriminant functions stored in the device, derived from analyses of groups of patients with known coronary artery disease and/or atrial or ventricular disease.

Figure 1:
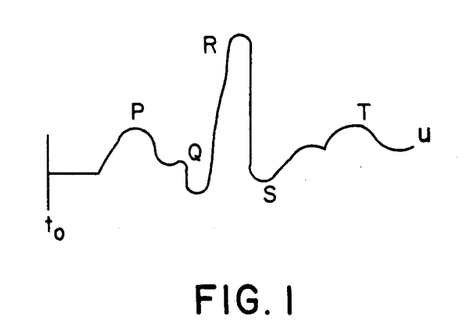
FIG. 1 is a diagram of a normal heart beat electrical waveform as seen at one lead of an ECG system.

A typical heart beat is shown in FIG. 1. It consists from left to right in FIG. 1 of an initial flat ("isoelectric") portion; a "P" wave; a negative "Q" wave; an "R" wave whose leading-upward slope is the depolarization wave and whose lagging-downward slope is the repolarization wave; a negative "S" wave; the "S-T" segment between S and T waves; the "T" wave and sometimes a final small "U" wave.

2. Placement of Electrodes and System Component Description

In the system of the present invention, a large number, at least 20 and preferably 32 to 64, of removable electrode contact leads are placed on the body surface of the patient covering both the chest and the back of the patient. In contrast, the conventional EKG system uses 12 leads, although the body surface mapping systems (e.g., HPM-51005 of Chunichi Denishi Co.) have used as many as 87 leads, or even 192 leads (LUX et al).

The system 10, as shown in FIG. 1, includes an EKG-multi-channel of N-channels, the number of channels being in the range of 32-64 channels. The number of channels is selected to be the number that accounts for 99.9% of the variance of the data on the body surface. The data consists typically of 1,000 heart beats, but, may be as small as one beat. Since the normal heart beat rate, at rest, is about 80 beats per minute, if there are no artifacts to disturb the collection of the data, the gathering of 1000 beats should take only 10-15 minutes. In many cases, a sample of 50 beats will suffice, and data collection will require less than one minute.

Figure 2:
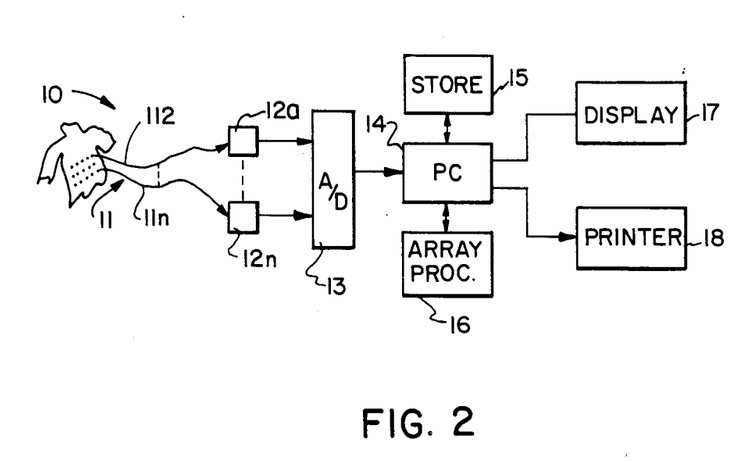
FIG. 2 is a schematic block drawing of the system of the present invention.

Each electrode lead II is connected in an individual separate channel. In FIG. 2 only two leads IIa and IIn are shown for simplicity of illustration, where n represents the last lead in the group preferably of from 20 to 64 leads.

Each ECG lead IIa-IIn is connected to low-noise amplifier 12$a$-$n$, within the order of 1 microvolt of noise and a band-width from 0-250 Hz. Those 12$a$-$n$ amplifiers are connected to an analog-to-digital converter 13 which samples at the millisecond rate (1000 samples/sec./channel). A typical storage, based upon 168 K-bytes per beat and 1000 beats is 168 million bytes.

The system in one preferred embodiment may utilize an IBM-AT or look-alike personal computer 14 with a 675K of RAM memory, digital storage at "store" 15 which is a 80 MB hard disk (200 MB perferred), an array processor 16, a high resolution CRT display monitor 17, and a color printer 18 for paper ("hard") copy.

3. Data Analysis, Feature Extraction and Statistical Evaluation

As shown in FIG. 2, the ECG electrodes produce N channels of digitized heart wave data 20 (EKGn). That data are transferred to bulk storage 21, preferably a "hard disk" (Winchester) or other medium, providing digital storage.

As shown in FIG. 2, the "Feature Detectors" 22 detect features such as the peak of the R wave and other peaks. Any detected peak may be selected by the user on the keyboard 14 to be the fiducial time, using the "Fiducial Time Selector" 23. This selection can be varied, as some diseases may be better detected with the selection of one portion of the heart beat as the fiducial mark than with another.

The data are then analyzed both in the time domain 24 and the frequency domain 25. The analysis in the two domains may be performed in sequence in the computer system, and will require on the order of 5-10 minutes after completion of collection of the largest samples envisaged and only 1-2 minutes in most cases.

The averaging process may, optionally, utilize a comb filter, as set forth in Dr. John's U.S. Pat. No. 4,705,049, incorporated by reference herein. That technique will optimize the signal-noise ratio to detect "small" (low signal) events.

A. Time Domain Analysis 24

Figure 3:
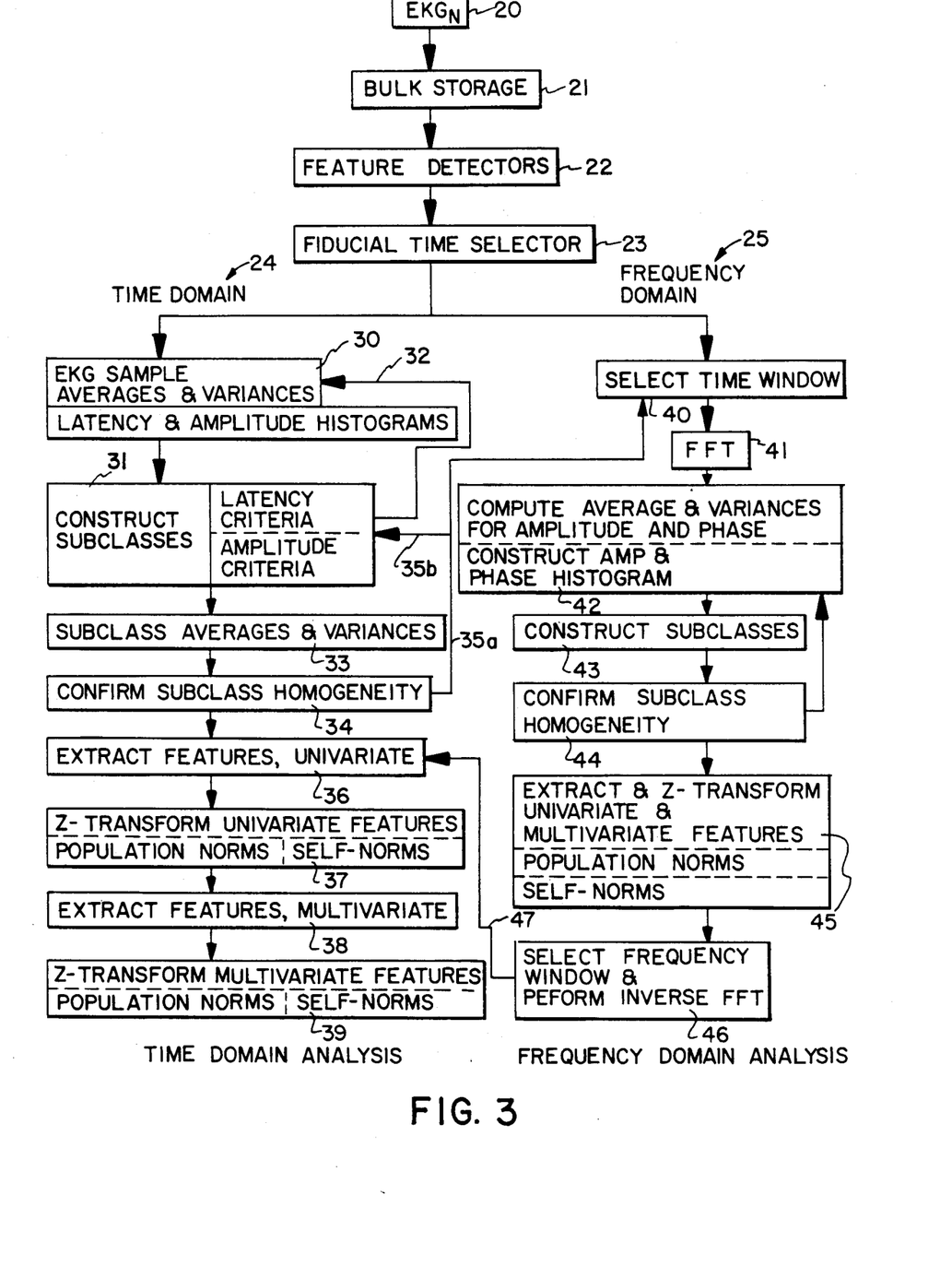
FIG. 3 is a block diagram showing the ECG waveform analysis and statistical system and method.

Using the selected fiducial time detected by fiducial time selector 23 on each beat, the average EKG and its variance, is computed for the whole data set collected at each electrode, by "EKG Sample Averager and Variances" 30. Although various fiducial times may be selected, only one fiducial time must be used for the entire electrode array during the computaion of averaged EKG's and variances, as well as for the computation of FFT's which will be discussed in the next section. During averaging, latency, duration, and amplitude histograms are constructed for selected features of the set being averaged, such as PQ, QR, RS, QS, ST, TU or other interval latencies or durations and P, R, T, U, QR, RS, ST or other peak amplitudes or amplitude differences.

Various criteria can now be applied to construct homogenous subclasses from what may be a heterogenous mixture of normal and abnormal individual beats in the whole data set. Such criteria include, but are not limited to, the requirement that the distribution of amplitudes at all latencies across the cardiac cycle (defined as the sequence of EKG voltages from the selected fiducial feature until the last time point 1 millisecond before recurrance of the fiducial time point, $t_o$) must be Gaussian and that the latency, duration, and amplitude histograms also be Gaussian. By examining all of these distributions for non-Gaussianity or "multi-modality" and for "outliers" outside the limits of the sample distribution, and by recursive analysis of variance techniques, and by such steps, for example, as dividing the whole sample into those beats lying in the upper or lower portion of a bimodal distribution, "Construct Subclasses" 31 parses the initial samples of beats into subgroups automatically or with operator supervision. These fractional samples are returned for iteration of average and variance and histogram computation 32. "Subclasses Averages and Variances" 33 are constructed and tested by "Confirm Subclass Homogeneity" 34. This process is iterated 35A if heterogeneity of variance is found in any subclass. When the initial sample has been divided into the smallest number of subclasses with homogeneity of variance, all beats in the initial sample are labeled to identify the subclass to which they belong. The full set of classified beats and the averaged EKG waveshapes of each sublcass identified for each electrode are the input 35B which is made available for frequency domain analysis 25.

The full set of classified beats, subclass averages, variances and histograms is also the input to "Extract Features, Univariate" 36. This extracts a wide variety of features including but limited to, the average R-R interval, QRS amplitued and power QR and RS power, etc., which characterize each of the subclasses of typical and "aberrant" beats idenfified in the data from each lead.

This full set of univariate features is now Z-tranformed by "Z-transform Univariate Features" 37 using the mean value and standard deviation of the distribution of each of these features obtained from normative studies of large samples of cardiac-healthy normal subjects of the same age and sex as the patient ("Population Norms") as well as the distribution of values observed in the most typical (largest) subclass of beats within the individual patient ("Self-Norms"), where Z-transform is defines as:

$$Z_\mu = (P_\mu - \overline{M}_\mu)/6_\mu \qquad \text{Eq. (1)}$$

which yields the univariate Z-score, $Z_\mu$, and $P_\mu$ = patient univariate feature value $\mu$, $\overline{M}_\mu$ = normative value of feature $\mu$, $6_\mu$ = standard deviation of reference norms for feature $\mu$.

Using this set of Z-transformed univariate features, composite or multivariate features which combine the information provided by one or several univariate features across various subsets of leads (such as "left front", "right front", "upper left quadrant", "lower left quadrant", and other lead combinations of interest such as, but not limited to, "whole body surface" are computed by "Extract Features, Multivariate" 38. This feature can be though of as "Heart State Vector" which measure the distance of the individual patient's heart from the origin of a multi-dimensional cardiopathology space in which each dimension corresponds to one of the univariate features. If these dimensions of the signal space were orthogonal, the length of the "Heart State Vector" would correspond to the *severity* of the multivariate abnormality. Further, the orientation of the Heart State Vector is expected to identify the *type* of coronary pathology.

The Euclidean length of the Heart State Vector, HSV, is:

$$HSV_i = \left| \sum_{i=1}^{n} Z_i^2 \right|^{\frac{1}{2}} \qquad \text{Eq. (2)}$$

where n is the number of univariate features in subset i.

However, the univariate features are inter-correlated, or "non-orthogonal". Therefore, it is necessary to compute the Mahalanobis length, M, which takes the covariance matrix of the feature subset into account.

It now becomes necessary to provide an acceptable metric for M. This is accomplished by Z-Transformation of Multivariate Features" 39 analogous to that described for univariate features in Eq. 1; that is, the multivariate Z-score, $Z_{Mi}$, is defined as:

$$Z_{Mi} = (M_i - \overline{M}_i)/6_i \qquad \text{Eq. (3)}$$

where
M = patient multivariate feature i
$\overline{M}$ = population or self-norm mean of multivariate feature i
6 = standard deviation of reference norms for multivariate feature i This completes the extraction and initial statistical evaluation of features in the time domain. These features are then subjected to spatio-temporal analysis and are dislplayed by the information enhancing techniques described in Section C below.

B. Frequency Domain Analysis

The same fiducial time (s) selected for analysis in the time domain, either raw EKG data 23 or averaged subclass EKG's 35B, is used in the frequency domain analysis. The whole period of the cardiac cycle, or any sub-period considered of special interest (e.g., the rising or falling portion of the QRS complex), is specified for analysis in the frequency domain by "Select Time Window" 40 and subjected to frequency analysis, separately for each lead, by the Fast Fourier Transform, or "FFT" 41. For each lead, the average amplitude and phase angle across the set of beats is computed separately for each frequency, in steps of 0.5 HZ from 0 to 250 HZ, by "Compute Average and Variances for Amplitude and Phase" 42. Histograms of the values of amplitude and phase are also constructed. This procedure is carried out separately for each subclass of beats identified in "Confirm Subclass Homegeneity" 34. Using methods analogous to those used for construction of homogenous subclasses in the time domain 31-34, the homogeneity of data from those subclasses is tested and confirmed in the frequency domain and additional subclasses constructed, if required, using "Compute Average and Variances For Amplitude and Phase" 42, "Constuct Subclasses" 43 and "Confirm Subclass Homogeneity" 44.

Using methods analogous to those described in the time domain for extraction and Z-transformation of univariate and multivariate features 36–39 against population and self-norms, univariate and multivariate features are extracted and Z-transformed in the frequency domain by "Extract and Z-Transform Univariate and Multivariate Features" 45.

Once these steps have been accomplished, it is impossible to identify frequency domains of particular interest because of the appearance of high Z-scores for the corresponding feature(s) in particular leads. Using these frequency windows, the Inverse Fourier Transform is performed by "Select Frequency Window and Perform Inverse FFT" 46. The result of this operation is to construct the EKG sub-waveshape which is the embodiment of the frequency domain features, identified as abnormal, transformed back into the time domain. These pathological (i.e., "improbable" waveshapes can be displayed (see Section C) or returned to the time domain algorithms for further analysis 47.

C. Spatio-temporal Analysis and Display Options

In both the time domain and the frequency domain, the univariate features described above quantify characteristics of the heart-generated potentials at specific points on the body surface. The multivariate features combine information about several characteristics of the potentials at a single place or about a single or multiple characteristic at several places. The latter kind of feature contains *implicit* information about some spatial relationships of potentials among different points on the body surface. Potentially, the most sensitive information about subtle changes in the heart may consist of changes in timing or voltage differences between different parts of the heart muscle which are not detectable in a single place along, but are reflected in the spatio-temporal patterns of potential changes on the body surface as a whole. For this reason, it is necessary to obtain *explicit* quantitative information about spatio-temporal body surface potential relationships.

Factor Analysis

Figure 4:
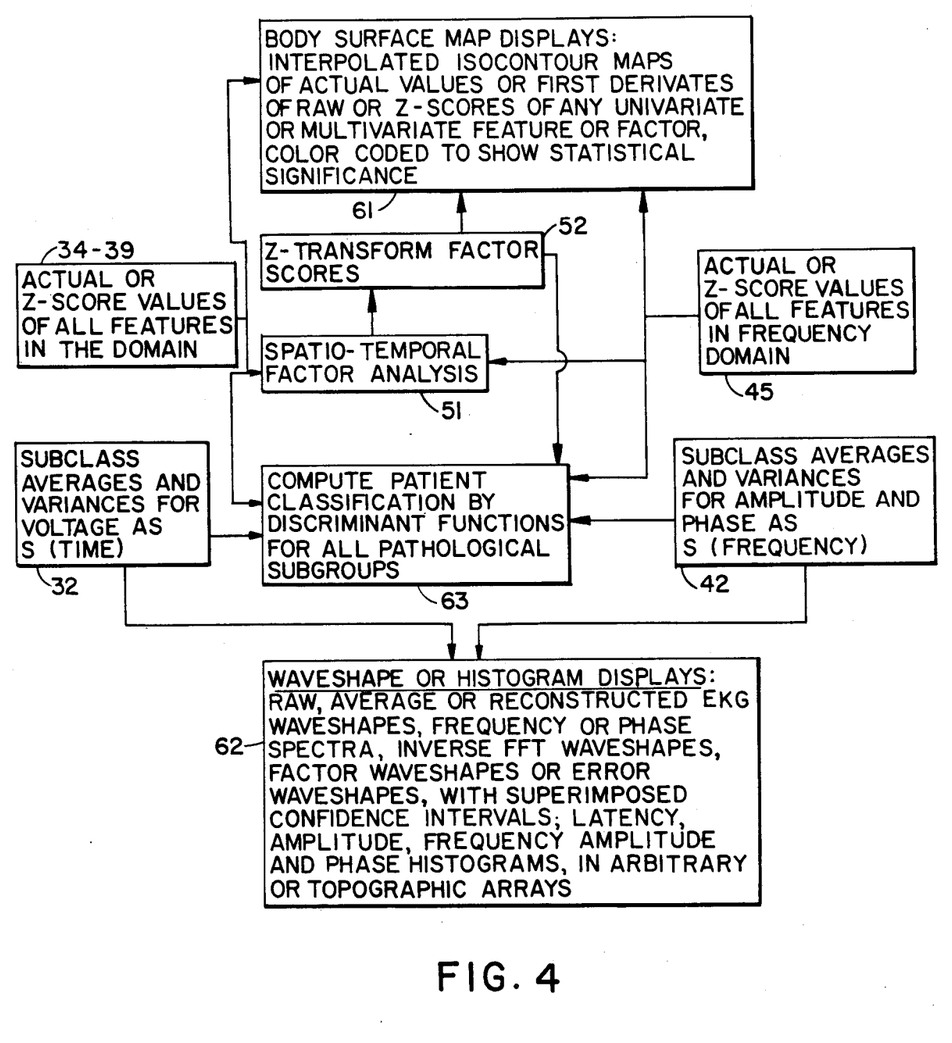
FIG. 4 is a block diagram showing the spatio-temporal (space-time) analysis and display options.

In order to accomplish this, the full set, for example, of 32 single or averaged EKG waveshapes or the full set of 32 frequency spectra (both amplitude and phase spectra) are subjected to principal components analysis, followed by a Varimax rotation using "Spatio-Temporal components analysis, followed by a Varimax rotation using "Spatio-Temporal Factor Analysis" 51. The effect of this is to obtain a set of *basis* functions ($F_j(t)$ in the time domain or $F_j(S)$ in the frequency domain) such that the EKG, waveshaped at any point i on the body surface, $EKG_i$, can be completely described either in the time domain or in the frequency domain by a weighted linear combination of these basis functions or *factors*. Thus, $$EKG_i = \sum_{j=1}^{k} a_{ij} F_j^{(t)} \qquad \text{Eq. (4)}$$

where
- $EKG_i$ = EKG at position i
- $a_{ij}$ = weighting coefficient denoting amount of factor j contributing to $EKG_i$
- $F_j^{(t)}$ = factor j
- K = number of factors in the time domain needed for accurate reconstruction of EKG.

Then, if the body surface is covered by an array of N electrodes, the N EKG signals can all be described by the following matrix:

$$
\begin{aligned}
EKG_1 &= a_{11} F_1 + a_{12} F_2 + \cdots + a_{1K} F_K + R_1 \\
&\vdots \\
EKG_N &= A_{N1} F_1 + a_{N2} F_2 + \cdots + A_{NK} F_K + R_N
\end{aligned}
\qquad \text{Eq. (5)}
$$

where $R_1$ = residual error of reconstruction of $EKG_i$.

Each factor contributes to the potential wave at every point on the body surface in an amount proportional to the weighting coefficient, or *factor score*. Each factor represents an extensive process in time. In fact, the factors yielded after the Varimax rotation resemble physiological processes such as a P-wave, an R-wave, a T-wave, etc. in the time domain or their Fourier-Transformed equivalent in the frequency domain. Thus, each factor describes a *spatio-temporal process* which arises from a set of electrical generators in the heart muscle. The full set of fluctuations of potential at which all points on the body surface which occur in time during the cardiac cycle can thus be understood as the properly weighted sum of these generators at each point. The residual error term, $R_i$, describes the extent of the inaccuracy in this description at any point i on the surface.

The anatomy and physiology of the heart in normal persons is extremely reproducible. Differences in body size and shape across individuals will produce differences in the absolute voltage amplitude of heart signals recorded at the body surface, which can be compensated for by normalization of amplitude across the total set of EKG signals within a patient to a constant, such as 100%. Differences in heart rate can be compensated for by time normalization such as, for example, setting the R-R interval or QRS *duration of all patients to a contant, such as* 100%, for morphology analysis and restoring the actual individual time compression or expansion. Factor analyses are performed on a large number of persons ascertained to be normal by the medical criteria available for cardiac function. For each factor score, $A_{ij}$, the mean value and standard deviation are obtained. These normative data are stored in the Heart State Analyzer using "Z-Transform Factor Scores" 52. It now becomes possible to Z-transform the individual factor score, $a_{aj}$, by Equation 1, such that:

$$EKG_i = \sum_{j=1}^{K} Z_{ij} F_j \qquad \text{Eq. (6)}$$

where $Z_{ij}$ = Z-score of factor score $a_{ij}$

Equation 6 may be analyzed in the space-time domain as follows:

$$
\begin{aligned}
EKG_1(t) &= Z_{11} F_1(t) + Z_{12} F_2(t) + \cdots + Z_{1K} F_N(t) \\
&\vdots \\
EKG_N(t) &= Z_{N1} F_1(t) + Z_{N2} F_2(t) + \cdots + Z_{NK} F_K(t)
\end{aligned}
$$

The corresponding equation in the space-frequency domain is:

$$EKG_i(f) = \sum_{X=1}^{Y} Z_{iX} F_X(f) \qquad (7)$$

where Y is the number of factors in the frequency domain needed to reconstruct all EKG: which may be analyzed as follows:

$$
\begin{aligned}
EKG_1(f) &= Z_{11} F_1(f) + Z_{12} F_2(f) + \cdots + Z_{1Y} F_Y(f) \\
&\vdots \\
EKG_X(f) &= Z_{N1} F_1(f) + Z_{N2} F_2(f) + \cdots + Z_{NY} F_M(f)
\end{aligned}
$$

The space-time and space-frequency domains are combined:

$$\text{For each } EKG: \left| \sum_{j=1}^{K} Z_{ij}^2 + \sum_{K=1}^{Y} Z_{ik}^2 \right|^{\frac{1}{2}} \quad (8)$$

(corrected for the intercorrelations between the $F_j(t)$ and the $F_Y(F)$).

Topographic Body Surface Maps 61

Using "Body Surface Map Displays" 61, topographic maps of body surface potentials can now be constructed for the anatomical distribution of actual EKG voltages during a single cardiac cycle, whether "raw" or averaged, and of space-time or space-frequency factor Z-scores, separately for each factor. Such maps can be color-coded for ease of interpretation, according to the statistical significance of the Z-score. For example, red colors signify excessive values and blue colors signify deficient values on such a color palette. Similar topographic maps are constructed for any raw or Z-transformed value of any univariate or multivariate feature, and are similarly color-coded to reflect intensity or statistical significance of the feature whether in the time or the frequency domain. We call such data representations "HEARTMAPS".

Waveshape or Histogram Displays 62

Using waveshape or histogram display 62, the operator can view raw, average or reconstructed EKG waveshapes, frequency or phase spectral contours, inverse FFT waveshapes, factor waveshapes, residual error waveshapes, with or without superimposed confidence intervals. Histograms of latencies or amplitudes or other features in the time domain, and of the amplitude, phase or other features in the frequency domain can also be displayed, either in arbitrary arrays or positioned on the body surface to indicate their anatomical location.

Special importance is given to the "relative phase" display, which shows the relative phase of any frequency component across the full set of recording electrodes. This display is particularly sensitive to small changes in the *relative speed* of depolarization or repolarization of different regions of the heart and reveals low levels of local ischemia. The relative phase display can be Z-transformed to show the significance of deviations from the differences in phase which are normally observed.

Discriminant Functions 63

Using groups of patients with single or multiple coronary artery disease, or other forms of atrial or ventricular dysfunction, samples of EKG are subjected to evaluation by the Heart State Analyzer. Discriminant functions are constructed which accurately classify individual members of groups suffering from various grades of occlusion of the right coronary artery, the left anterior descending coronary artery, the circumflex artery or other patterns of coronary artery disease and ventricular and atrial dysfunction. These discriminant functions are stored in the Heart State Analyzer. The probability that any one of these diseases is present is assessed, together with an estimate of the extent of the disease, that is, degree of stenosis of the involved vessels or other abnormal ECG activity.

Using "Compute Patient Classification by Discriminant Functions" 63 the data from an individual patient are compared with the patterns found distinctive for these various major categories of coronary artery disease. The probability that any one of these diseases is present is assessed, together with an estimate of the extent of the disease, that is, degree of stenosis of the involved vessels.

What is claimed is:

1. An electrocardiographic system for the detection of heart disease in a patient including:
   at least 20 electrodes to detect heart beat activity analog electrical signals, adapted to be removably connected to the skin of the patient in separated locations around the heart on the chest, sides and back of the patient (torso);
   amplification means to amplify the analog electrical signals detected at each electrode;
   digital conversion means to convert the said amplified electrical signals into EKG patient digital data;
   norm storage means to receive and store normative EKG digital data representing normal heart activity electrical signals and features extracted from such signals during the time of the cardiac cycle;
   digital computer statistical analysis means comprising space-time domain analysis means space-time domain and space-frequency domain analysis means to analyze the said patient digital data on a statistical basis compared to said stored normative data;
   said space-frequency domain analysis means including Fourier transform (FT) means for performing from 0 to 250 Hz a fourier transform of the patient digital data to form FT transformed data; subclass means to form homogenous subclasses of heart beats using the Fourier transform transformed data; transform means to statistically compare said subclasses with said normative data to produce transformed Fourier transform data; inverse Fourier transform means to inverse fourier transform said transformed Fourier transform data to produce inverse Fourier transform data;
   said space-time domain analysis including means to form homogenous subclasses of EKG waveshapes and transform means to statistically compare said patient digital data with said normative data in each subclass;
   topographic map display means to display the results of said statistical analysis of the signals from each electrode on a topographic map representing the chest, sides and back of the patient, each map location corresponding to the location of corresponding connected electrode; and
   means to classify the type of coronary artery disease by computing discriminant functions.

2. An electrocardiographic system to detect heart beats having P, Q, R, S, T and U portions as well as those containing some but not all P, Q, R, S and T portions including:
   a plurality of electrodes to detect heart activity electrical analog signals adapted to be removably connected to the skin of the patient in separated locations around the heart on the chest, sides and back of the patient (torso);
   amplification means to amplify the electrical signals detected at each electrode;
   digital conversion means to convert the said amplified electrical signals into EKG patient digital data;
   normative storage means to receive and store normal and abnormal digital data representing normal and abnormal heart activity electrical signals during the time of the cardiac cycle;

statistical analysis computer means comprising space-time domain analysis means to analyze the said EKG patient digital data on a statistical basis compared to said stored normal and abnormal data;

said space-time domain analysis means including means to construct homogenous subclasses; means to extract univariate features selected from the group consisting of the P-Q, Q-R, R-S, S-T, T-U or R-R portions; P, QRS, T or U amplitudes; and P, QR, QRS, T or U powers;

means to obtain factor scores of said univariate features and to Z-transform said factor scores as compared to said normal data to form factor Z-scores; said Z-transform being defined as:

$$Z_{ij} = \frac{P_{ij} - \overline{M}_{ij}}{\sigma_{ij}}$$

where as $Z_{ij}$ is the Z-score of factor score $a_{ij}$; $P_{ij}$ is patient weighting coefficient denoting the amount of factor j contributing to the EKG wave $EKG_i$; $\overline{M}_{ij}$ is the normal data weighting coefficient denoting the amount of factor j contributing to the EKG wave $EKG_i$ and $\sigma_{ij}$ is the standard deviation of the normative data for the factor j contribution to EKG wave $EKG_i$, topographic map display means to display the said factor Z-scores on a topographic map representing the torso of the patient, each map location corresponding to the location of a connected electrode.

3. An electrocardiographic system to detect heart beats having P, Q, R, S, T and U portions, as well as those beats having some but not all of said portions, for the detection of heart disease in a patient including;

at least 20 electrodes to detect heart beat activity electrical analog signals adapted to be removably connected to the skin of the patient in separated locations around the heart on the chest, sides and back of the patient (torso);

amplification means to amplify the electrical signals detected at each electrode;

digital conversion means to convert the said amplified electrical signals into ECG patient digital data;

normative storage means to receive and store normal digital data representing normal heart activity electrical signals during the time of the cardiac cycle;

digital computer statistical analysis means comprising space-time domain analysis means to analyze the said patient digital data on a statistical basis compared to said stored normal data;

said space-time domain analysis means including means to construct homogenous subclasses of heart beats; means to extract univariate features selected from the group consisting of the P-Q, Q-R, R-S, S-T, T-U, or R-R portions, P, QRS, T or U amplitude, P, QR, RS, QRS, T or U power;

means to obtain factor scores of said univariate features and to Z-transform said factor scores and compare to said normal data to form factor Z-scores;

where said means to obtain factor scores $a_{ij}$ operates in accordance with the equation $$EKG_i(t) = \sum_{i=1}^{K} a_{ij} F_j(t)$$

where $EKG_i$ is the voltage of the cardiac cycle seen at any position i;

$a_{ij}$ is the factor score defining the contribution of factor j to $EKG_{ij}$;

$F_j(t)$ is the waveshape of factor j throughout the cardiac cycle; and, where said Z-transform is defined as:

$$Z_{ij} = \frac{P_{ij} - M_{ij}}{\sigma_{ij}}$$

where as $Z_{ij}$ is the Z-score of factor score $a_{ij}$; $P_{ij}$ is patient factor score (weighting coefficient) denoting the amount of factor j contributing to the EKG wave $EKG_i$; $M_{ij}$ is the normal data weighting coefficient denoting the average amount of factor j normally contributing to the EKG wave $EKG_i$ and $\sigma_{ij}$ is the standard deviation of the normal data for the factor j contribution to EKG wave $EKG_{ij}$, and display means to display the said factor Z-scores on a topographic map representing the torso of the patient, each map location corresponding to the location of the corresponding electrode.

4. An electrocardiographic system as in claims 1, 2 or 3 and further including multivariate extraction feature means to form a heart state vector calculated from the Mahalanobis length which takes account of the covariance matrix of the features extracted by said multivariate extraction feature means.

5. An electrocardiographic system as in claims 1, 2 or 3 and further including multivariate extract feature means to form a heart state vector and Z-transformation means operatable with multi-variant feature means to Z-transform the multi-variant features and form a multivariate Z-score.

6. An electrocardiographic system as in claims 1, 2 or 3 wherein the number of electrodes is in the range of 20–64, each electrode being connected to a separate communication channel.

7. An electrocardiographic system as in claims 1, 2 or 3 wherein said normative data consists of data from a normal population without evidence of heart disease by current standards.

8. An electrocardiographic system as in claims 1, 2 or 3 wherein said display means includes a monitor and the statistical results are expressed in colors representing positive and negative abnormality and the extent thereof.

9. An electrocardiographic system as in claims 1, 2 or 3 wherein said system also includes fiducial selection means permitting the operator to select the portion of the heart wave which acts as a fiducial time for the analysis.

10. An electrocardiographic system as in claim 1 wherein said frequency domain transform means and time domain transform means perform (based on) Z-transformations.

11. An electrocardiographic system as in claim 10 wherein said heart activity is of heart beats having P, Q, R, S, T and U portions and said space-frequency domain analysis means further includes feature extraction means to extract features from the Z-transformed FT data, said features being selected from the group consisting of the average R-R interval, QRS amplitude, QRS power, QR power and RS power.

12. An electrocardiographic system as in claim 10 and further including means to calculate the principal components of frequency spectra to obtain a factor analysis of the IFT data and produce factor analysis scores therefrom and means to calculate the Z-transformations of the said factor analysis scores.

13. The method of electrodcardiograph EKG examination of a patient for the detection of heart disease including but not limited to the steps of:
removably connecting at least 20 electrodes to detect heart activity electrical signals to the skin of the patient in separated locations around the heart on the chest, sides and back of the patient (torso);
amplifying the analog electrical signals detected at each electrode;
converting the said amplified analog electrical signals into patient EKG digital data;
receiving and storing normal and abnormal digital ECG data representing normal and abnormal heart activity electrical signals during the time of the cardiac cycle;
automatically statistically analyzing the patient EKG data in computer means, in both the space-time domain and space-frequency domain, compared to said stored normal data;
said space-frequency domain analysis including performing a fourier transform of the data to form FT transformed data; forming homogenous subclasses of the FT transformed data; Z-transforming said FT transformed data; inverse fourier transforming said Z transformed FT data;
said space-time domain analysis including forming homogenous subclasses and comparing the patient data with the normal data in each subclass and Z transforming the comparison results; and
displaying the results of said space-frequency domain analysis and said space-time domain analysis of the signals from each electrode on a topographic map representing the torso of the patient, each map location corresponding to the location of the corresponding electrode.

14. An electrocardiographic method as in claim 13 wherein the number of electrodes is in the range of 20-64, each electrode being connected to a separate communication channel.

15. An electrocardiographic method as in claim 13 wherein the digital conversion step includes sampling at least at the millisecond rate in each channel.

16. An electrocardiographic method as in claim 13 wherein said normative data consists of data from a normal population without evidence of heart disease by current standards.

17. An electrocardiographic method as in claim 13 wherein said normal data consists of self-norm data obtained from said patient, which may include abnormal EKG patterns.

18. An electrocardiographic method as in claim 13 wherein the frequency domain analysis and time domain analysis results are expressed in color representing positive and negative abnormality and the extent thereof.

19. An electrocardiographic method as in claim 13 wherein said method also includes the step of selecting the portion of the heart wave which acts as a fiducial time for the analysis.

20. An electrocardiographic method as is claim 13 wherein said heart activity is of heart beats having P, Q, R, S, T and U portions and said space-frequency domain analysis further includes the step of extracting features from the Z-transformed FT data; said features being selected from the group consisting of the average R-R interval, QRS amplitude, QRS power, QR power and RS power.

21. An electrocardiographic method as in claim 13 and further including inverse Fourier transforming the data and producing IFT data and analyzing the IFT data to produce factor scores and to Z transform the said factor scores.

22. An electrocardiographic method as in claim 13 wherein said space-time domain analysis incudes computing subclasses and computing the average and variances in each subclass.

23. An electrocardiographic method as in claim 13 wherein said space-time domain analysis includes the step of extracting features of said heart beat electrical activity and the variances of said features.

* * * * *

UNITED STATES PATENT OFFICE
CERTIFICATE OF CORRECTION

Patent No. 4,974,598     Dated  December 4, 1990

Inventor(s)   ERWIN R. JOHN

It is certified that error appears in the above-identified patent and that said Letters Patent is hereby corrected as shown below:

Column 5, line 18, change "artial" to --arterial--;

Column 7, line 2, change "fractional" to --fractionated--;

Column 7, line 18, insert --not-- before "limited";

Column 7, line 19, change "amplitued" to --amplitude--;

Column 7, line 31, change "defines" to --defined--;

Column 8, line 20, change "dislplayed" to --displayed--;

Column 8, line 56&57 change "impossible" to --possible--;

Column 11, line 7, change "Fy(F)" to --Fy ($\mathcal{F}$) --;

Column 12, line 36, after "transform" insert --FT--;

Column 12, line 49, after "of" insert --a--;

Signed and Sealed this

Twenty-first Day of July, 1992

Attest:

DOUGLAS B. COMER

Attesting Officer     Acting Commissioner of Patents and Trademarks